(12) United States Patent
Banavali et al.

(10) Patent No.: US 7,635,596 B2
(45) Date of Patent: Dec. 22, 2009

(54) METHOD FOR MONITORING DEGRADATION OF LUBRICATING OILS

(75) Inventors: Rajiv Manohar Banavali, Rydal, PA (US); Kim Sang Ho, Richboro, PA (US)

(73) Assignee: Rohm and Haas Company, Philadelphia, PA (US)

( * ) Notice: Subject to any disclaimer, the term of this patent is extended or adjusted under 35 U.S.C. 154(b) by 668 days.

(21) Appl. No.: 11/269,788

(22) Filed: Nov. 8, 2005

(65) Prior Publication Data

US 2006/0128025 A1 Jun. 15, 2006

Related U.S. Application Data

(60) Provisional application No. 60/636,153, filed on Dec. 15, 2004.

(51) Int. Cl.
G01N 21/75 (2006.01)
C10G 1/00 (2006.01)
C10M 169/04 (2006.01)

(52) U.S. Cl. .................. 436/166; 508/110; 208/428; 507/907

(58) Field of Classification Search .............. 436/166
See application file for complete search history.

(56) References Cited

U.S. PATENT DOCUMENTS

| | | | |
|---|---|---|---|
| 2,611,772 A | 9/1952 | Allen et al. | |
| 2,727,045 A | 12/1955 | McSheahy | |
| 3,164,449 A | 1/1965 | Buxbaum et al. | |
| 4,755,012 A | 7/1988 | Kojima | |
| 5,342,974 A | 8/1994 | Ohyama et al. | |
| 5,525,516 A | 6/1996 | Krutak et al. | |
| 5,663,386 A | 9/1997 | Raulfs et al. | |
| 5,804,447 A | 9/1998 | Albert et al. | |
| 6,274,381 B1 | 8/2001 | Pauls et al. | |
| 6,312,958 B1 | 11/2001 | Meyer et al. | |
| 6,811,575 B2 * | 11/2004 | Ho et al. ................... | 8/521 |
| 2004/0106526 A1* | 6/2004 | Baxter et al. ............. | 508/256 |

FOREIGN PATENT DOCUMENTS

| | | | |
|---|---|---|---|
| EP | 0 201 368 | 3/1986 | |
| EP | 1323811 A2 * | 7/2003 | |
| EP | 1 426434 | 6/2004 | |
| EP | 1 479749 | 11/2004 | |
| EP | 1 486554 | 12/2004 | |
| JP | 61-246258 | 11/1986 | |
| JP | 61-291652 | 12/1986 | |
| JP | 62-015260 | 1/1987 | |
| JP | 11 281640 | 1/2000 | |

OTHER PUBLICATIONS

U.S. Appl. No. 10/308,618, filed Dec. 3, 2002, Chen et al.
U.S. Appl. No. 10/857,394, filed May 28, 2004, Baxter et al.
Standard Practice for Condition Monitoring of Used Lubricants by Trend Analysis Using Fourier Transform Infrared . . . , American Society for Testing and Materials (ASTM) D2412, Jun. 2002.

* cited by examiner

*Primary Examiner*—Sam P Siefke
*Assistant Examiner*—Bryan T Kilpatrick
(74) *Attorney, Agent, or Firm*—Kenneth Crimaldi

(57) ABSTRACT

A method for monitoring degradation of lubricating oils. The method comprises steps of: (a) adding to a lubricating oil at least one compound having formula (I)

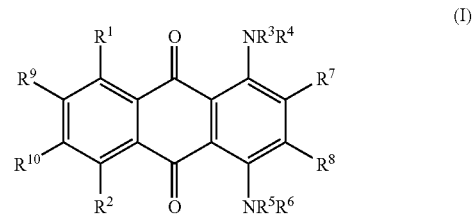

wherein $R^1$ and $R^2$ independently are hydrogen, hydroxy, $OR^{11}$, amino or $NR^{11}R^{12}$; $R^3$ and $R^5$ independently are alkyl, aryl, aralkyl, heteroalkyl or heterocyclic; $R^4$ and $R^6$ independently are hydrogen or alkyl; $R^7$, $R^8$, $R^9$ and $R^{10}$ independently are cyano, nitro, amide, carboxyl, ester, alkyl or hydrogen; $R^{11}$ is alkyl, aryl, aralkyl, heteroalkyl, heterocyclic or alkanoyl; $R^{12}$ is hydrogen or alkyl; provided that said at least one compound of formula (I) has at least one substituent selected from among cyano, nitro, hydroxy, hydroxyalkyl, amide, carboxyl, ester and unsaturated alkyl; and (b) measuring a spectroscopic property of the oil to determine degradation of said at least one compound.

10 Claims, No Drawings

METHOD FOR MONITORING DEGRADATION OF LUBRICATING OILS

CROSS REFERENCE TO RELATED PATENT APPLICATIONS

This is a non-provisional application of prior pending U.S. provisional Application Ser. No. 60/636,153 filed on Dec. 15, 2004.

BACKGROUND

This invention relates generally to a method for monitoring the degradation of lubricating oils.

Lubricating oils degrade at the high temperatures at which they often are used. A method for measuring the extent of degradation of a lubricating oil would allow timely replacement of degraded lubricants, resulting in cost savings.

Substituted dicyanoanthraquinones, including the following structure,

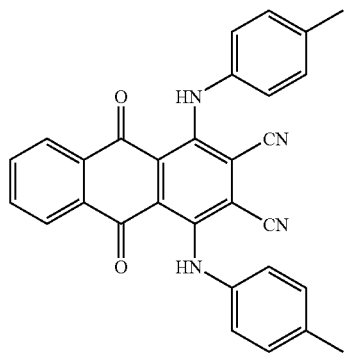

were disclosed in Japanese Patent Application JP61-246258 as colorants for an optical filter. This reference, however, does not suggest a method for monitoring degradation of lubricating oils. The problem addressed by this invention is to find a method for monitoring the degradation of lubricating oils.

STATEMENT OF INVENTION

The present invention is directed to a method for monitoring degradation of lubricating oils. The method comprises steps of: (a) adding to a lubricating oil at least one compound having formula (I)

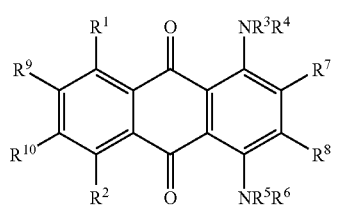

wherein $R^1$ and $R^2$ independently are hydrogen, hydroxy, $OR^{11}$, amino or $NR^{11}R^{12}$; $R^3$ and $R^5$ independently are alkyl, aryl, aralkyl, heteroalkyl or heterocyclic; $R^4$ and $R^6$ independently are hydrogen or alkyl; $R^7$, $R^8$, $R^9$ and $R^{10}$ independently are cyano, nitro, amide, carboxyl, ester, alkyl or hydrogen; $R^{11}$ is alkyl, aryl, aralkyl, heteroalkyl, heterocyclic or alkanoyl; $R^{12}$ is hydrogen or alkyl; provided that said at least one compound of formula (I) has at least one substituent selected from among cyano, nitro, hydroxy, hydroxyalkyl, amide, carboxyl, ester and unsaturated alkyl; and (b) measuring a spectroscopic property of the oil to determine degradation of said at least one compound.

DETAILED DESCRIPTION

All percentages are weight percentages, unless otherwise indicated. Concentrations in parts per million ("ppm") are calculated on a weight/volume basis. When a solvent is not specified for measurement of an absorption maximum, a hydrocarbon solvent is preferred. Extinction values are determined by measuring absorption in absorbance units ("AU") with a 1 cm path length on 10 mg/L solutions. A "lubricating oil" is a natural or synthetic oil, or a mixture thereof, having suitable viscosity for use as a lubricant, e.g., as crankcase oil in an internal combustion engine, automatic transmission fluid, turbine lubricant, gear lubricant, compressor lubricant, metal-working lubricant, hydraulic fluid, etc. An "alkyl" group is a hydrocarbyl group having from one to twenty carbon atoms in a linear, branched or cyclic arrangement. Alkyl groups optionally have one or more double or triple bonds. Substitution on alkyl groups of one or more halo, hydroxy, alkoxy, cyano, nitro, ester, amide or carboxyl groups is permitted; these substituents may in turn be substituted by one or more halo or hydroxy substituents where possible. Preferably, alkyl groups have no halo substituents, and in one preferred embodiment, alkyl groups are saturated, and most preferably, unsubstituted. A "heteroalkyl" group is an alkyl group in which at least one carbon has been replaced by O, NR, or S, wherein R is hydrogen, alkyl, aryl or aralkyl. An "aryl" group is a substituent derived from an aromatic hydrocarbon compound. An aryl group has a total of from six to twenty ring atoms, and has one or more rings which are separate or fused. An "aralkyl" group is an "alkyl" group substituted by an "aryl" group. A "heterocyclic" group is a substituent derived from a heterocyclic compound having from five to twenty ring atoms, at least one of which is nitrogen, oxygen or sulfur. Preferably, heterocyclic groups do not contain sulfur. Substitution on aryl or heterocyclic groups of one or more of the following groups: halo, cyano, nitro, hydroxy, ester, amide, carboxyl, alkoxy, alkyl, heteroalkyl, alkanoyl, amino, or amino substituted by one or more of alkyl, aryl, aralkyl, heterocyclic, heteroalkyl or alkanoyl is permitted, with substitution by one or more halo groups permitted on substituents where possible. Preferably, aryl and heterocyclic groups do not contain halogen atoms. In one preferred embodiment of the invention, aryl and heterocyclic groups are unsubstituted or substituted only by alkyl groups. An "aromatic heterocyclic" group is a heterocyclic group derived from an aromatic heterocyclic compound.

In one embodiment of the invention, $R^4$ and $R^6$ are hydrogen; in another embodiment, $R^4$ and $R^6$ are alkyl, preferably $C_1$-$C_4$ saturated unsubstituted acyclic alkyl. In one embodiment of the invention, $R^3$, $R^5$ and $R^{11}$ in formula (I) are alkyl, aryl or aromatic heterocyclic. Preferably, $R^3$ and $R^5$ represent the same substituent. In one embodiment of the invention, $R^3$ and $R^5$ are aryl substituted by at least one $C_2$-$C_{20}$ alkyl group or aromatic heterocyclic substituted by at least one $C_2$-$C_{20}$ alkyl group; alternatively, $R^3$ and $R^5$ are aryl substituted by at least one $C_4$-$C_{20}$ alkyl group or aromatic heterocyclic substituted by at least one $C_4$-$C_{20}$ alkyl group; preferably $R^3$ and $R^5$ are phenyl substituted by at least one $C_2$-$C_{20}$ alkyl group, more preferably by at least one $C_4$-$C_{20}$ alkyl group. When $R^3$ and $R^5$ are aryl or aromatic heterocyclic groups, preferably $R^4$ and $R^6$ are hydrogen.

In one embodiment of the invention, $R^3$ and $R^5$ are alkyl, preferably $C_2$-$C_{20}$ alkyl, more preferably $C_4$-$C_{20}$ alkyl; preferably $R^3$ and $R^5$ are saturated unsubstituted alkyl. In one embodiment of the invention, $R^3$ and $R^5$ are $C_5$-$C_8$ cyclic alkyl groups; preferably $R^3$ and $R^5$ are saturated unsubstituted $C_5$-$C_8$ cyclic alkyl groups and $R^4$ and $R^6$ are hydrogen. In one preferred embodiment, $R^3$ and $R^5$ are cyclohexyl. In another preferred embodiment, $R^3$ and $R^5$ are $C_5$-$C_8$ cyclic alkyl groups, $R^4$ and $R^6$ are hydrogen, and $R^1$ and $R^2$ are $NR^{11}R^{12}$, where $R^{12}$ is hydrogen and $R^{11}$ is $C_5$-$C_8$ cyclic alkyl, preferably saturated unsubstituted alkyl; preferably $R^3$ and $R^5$ are cyclohexyl and $R^1$ and $R^2$ are cyclohexylamino.

In another preferred embodiment, $R^3$ and $R^5$ are aryl substituted by at least one $C_2$-$C_{20}$ alkyl group or aromatic heterocyclic substituted by at least one $C_2$-$C_{20}$ alkyl group, $R^4$ and $R^6$ are hydrogen, and $R^1$ and $R^2$ are $NHR^{11}$, where $R^{11}$ is aryl substituted by at least one $C_2$-$C_{20}$ alkyl group or aromatic heterocyclic substituted by at least one $C_2$-$C_{20}$ alkyl group. In one embodiment, $R^7$, $R^8$, $R^9$ and $R^{10}$ are cyano or hydrogen. In one embodiment, $R^7$, $R^8$, $R^9$ and $R^{10}$ all represent cyano. In one embodiment, $R^7$ and $R^8$ represent cyano, and $R^9$ and $R^{10}$ are hydrogen. Preferably, $R^1$ and $R^2$ independently are hydrogen, hydroxy or $NR^{11}R^{12}$. Preferably, $R^{11}$ is alkyl or aryl. In one preferred embodiment of the invention, $R^{11}$ is $C_2$-$C_{20}$ alkyl. Preferably, $R^1$ and $R^2$ represent the same substituent. Most preferably, $R^1$ and $R^2$ represent hydrogen or $NR^{11}R^{12}$. In one embodiment, $R^1$ and $R^2$ are $NR^{11}R^{12}$, and $R^3$, $R^4$, $R^5$, $R^6$, $R^{11}$ and $R^{12}$ are alkyl, preferably the same alkyl group; in one preferred embodiment, $R^3$, $R^4$, $R^5$, $R^6$, $R^{11}$ and $R^{12}$ are $C_1$-$C_4$ saturated unsubstituted acyclic alkyl groups, and most preferably, methyl groups.

In one embodiment, a compound of formula (I) is substituted by at least one group selected from among $C_2$-$C_{20}$ unsubstituted saturated acyclic alkyl groups, aryl groups substituted by at least one $C_2$-$C_{20}$ alkyl group, aromatic heterocyclic groups substituted by at least one $C_2$-$C_{20}$ alkyl group and $C_5$-$C_8$ cyclic alkyl groups. Alternatively, a compound of formula (I) is substituted by at least two groups selected from among $C_2$-$C_{20}$ unsubstituted saturated acyclic alkyl groups, aryl groups substituted by at least one $C_2$-$C_{20}$ alkyl group, aromatic heterocyclic groups substituted by at least one $C_2$-$C_{20}$ alkyl group and $C_5$-$C_8$ cyclic alkyl groups.

A compound of formula (I) has at least one substituent selected from among cyano, nitro, hydroxy, hydroxyalkyl, amide, carboxyl, ester and unsaturated alkyl. Preferably, a substituent is present which is selected from among cyano, nitro, carboxyl and hydroxyalkyl, and which is present either on the anthraquinone ring, as at least one of $R^7$, $R^8$, $R^9$ and $R^{10}$; or it is present as a substituent on one or more of the $R^3$, $R^4$, $R^5$, $R^6$, $R^{11}$ and $R^{12}$ groups in the compound. Hydroxyalkyl groups are alkyl groups substituted by at least one hydroxy group, and optionally with other groups as well. In one embodiment, hydroxyalkyl groups have no non-hydroxy substituents. Amide and ester substituents are attached at either end, e.g., both —C(O)NR$_2$ and —NRC(O)R are amide substituents, and both —C(O)OR and —OC(O)R are ester substituents; where "R" groups are the same or different, and represent any organic substituent groups. In one embodiment, "R" groups in amide substituents are alkyl or hydrogen, and those in ester groups are alkyl.

In one preferred embodiment of the invention, $R^7$ and $R^8$ are cyano, $R^4$ and $R^6$ are hydrogen, $R^9$ and $R^{10}$ are hydrogen, and a compound of formula (I) has formula (II)

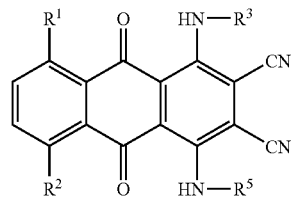

In another preferred embodiment of the invention, $R^7$ and $R^8$ are cyano, $R^4$ and $R^6$ are hydrogen, $R^9$ and $R^{10}$ are hydrogen, $R^1$ and $R^2$ are hydrogen, and a compound of formula (I) has formula (III)

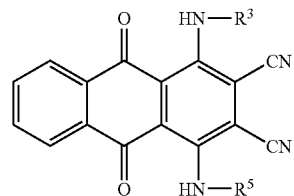

In another preferred embodiment of the invention, $R^7$ and $R^8$ are cyano, $R^4$ and $R^6$ are hydrogen, $R^9$ and $R^{10}$ are hydrogen, $R^1$ and $R^2$ are $NHR^{11}$, and a compound of formula (I) has formula (IV)

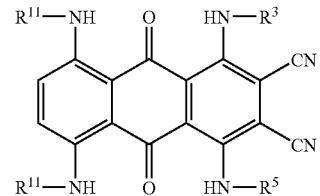

In another preferred embodiment of the invention, $R^7$, $R^8$, $R^9$ and $R^{10}$ are cyano, $R^1$ and $R^2$ are $NHR^{11}$, $R^4$ and $R^6$ are hydrogen, and a compound of formula (I) has formula (V).

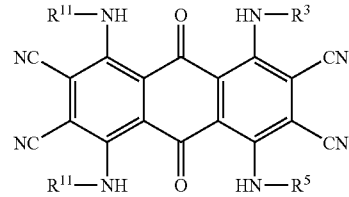

Preferably the amount of each compound of formula (I) added to the lubricating oil is at least 0.5 ppm, more preferably at least 1 ppm, more preferably at least 5 ppm, more preferably at least 10 ppm, and most preferably at least 100 ppm. Preferably the amount of each compound is less than 10,000 ppm, more preferably less than 5,000 ppm, more preferably less than 2,000 ppm and most preferably less than 1,000 ppm.

A spectroscopic property of the lubricating oil is absorption of electromagnetic radiation in a particular frequency range, or fluorescent emission. Preferably, amounts of compounds of formula (I) are measured by determining a spectroscopic property of the oil by exposing it to electromagnetic radiation having wavelengths in the portion of the spectrum containing the absorption maxima of the compound of formula (I), and detecting the absorption of light or fluorescent emissions. It is preferred that the detection equipment is capable of calculating concentrations and concentration ratios in a lubricating oil. Typical spectrophotometers known in the art are capable of detecting the compounds used in the method of this invention when they are present at a level of at least 0.5 ppm. It is believed that compounds of formula (I) degrade under conditions encountered in use of lubricating oils, and that measurement of the extent of that degradation by spectroscopic analysis provides useful information about the extent of degradation of the lubricating oil itself. In one embodiment, the preferred cyano, nitro, hydroxy, hydroxyalkyl, amide, carboxyl, ester and unsaturated alkyl substituents degrade to other substituents having different spectroscopic characteristics, e.g., infrared (IR) and near-infrared (NIR) absorption frequencies. Preferably, absorption is measured in the mid-IR range, i.e., from 1500 to 2250 $cm^{-1}$, or in the NIR range from 700 to 1000 nm. For example, comparison of the IR absorption intensity displayed by one of these substituents at one of its characteristic absorption frequencies with the intensity of that substituent when the compound was first introduced into the lubricating oil allows a determination of the fraction of molecules containing the substituent that have been degraded, and this in turn can be correlated with the degradation of the oil. For example, a cyano substituent could by hydrolyzed under operating conditions, first to an amide, and then to a carboxyl group. As the hydrolysis progresses, the characteristic IR absorption of the cyano substituent in the area of 2200 to 2250 $cm^{-1}$ would gradually decrease in intensity, allowing the hydrolysis of the cyano group to be monitored.

In one embodiment of the invention, at least one compound of formula (I) is formulated in a solvent to facilitate its addition to the lubricating oil. The preferred solvents for substituted anthraquinone dyes are N-methylpyrrolidinone, N,N-dimethyl propylene urea, nitrobenzene, toluene, N,N-dimethylformamide and 2-sec-butylphenol. Preferably, the dye is present in the solvent at a concentration of from 0.1% to 10%.

Compounds of formula (I) also can act as markers for the lubricating oil to provide information about the oil, for example, the identity of its manufacturer. Detection of the compounds advantageously could be done by near-IR spectral analysis to take advantage of this relatively clear region in the absorption spectrum of a lubricating oil. For example, measurement of near-IR absorption in the 650 nm to 950 nm range could be used to detect the compounds.

EXAMPLES

Example 1

Synthesis of
1,4-di-(n-butylamino)-2,3-dicyanoanthraquinone.

A mixture of 25.7 parts of Solvent Blue 35 {1,4-di-(n-butylamino)-anthraquinone}, 14.8 parts of NaCN, 10 parts of $NH_4HCO_3$, and 100 parts of dimethyl sulfoxide (DMSO) was allowed to react at 90-95° C. for 6 hours to give 1,4-di-(n-butylamino)-2,3-dicyanoanthraquinone. This material has a maximum absorption band ($\lambda_{max}$) at a wavelength of 700 nm in xylene with an extinction value of 0.23 AU for 10 mg/L.

Example 2

Synthesis of 1,4,5,8-tetra-(4'-n-butylphenylamino)-2,3-dicyanoanthraquinone and 1,4,5,8-tetra(4'-n-butylphenylamino)-2,3,6,7-tetracyanoanthraquinone A mixture of 8.0 parts of 1,4,5,8-tetra(4'-n-butylphenylamino)anthraquinone, 2.53 parts of NaCN, 1.65 parts of $NH_4HCO_3$, and 39 parts of DMSO was allowed to react at 90-95° C. for 6 hours to give 1,4,5,8-tetra-(4'-n-butylphenylamino)-2,3-dicyanoanthraquinone. The structure of the di-cyano product was confirmed by proton and carbon-13 NMR. This material has a maximum absorption band ($\lambda_{max}$) at a wavelength of 835 nm in xylene with an extinction value of 0.342 AU for 10 mg/L. Longer reaction time also gave rise to the 1,4,5,8-tetra(4'-n-butylphenylamino)-2,3,6,7-tetracyanoanthraquinone. The structure of the tetra-cyano product also was confirmed by proton and carbon-13 NMR. This material has a maximum absorption band ($\lambda_{max}$) at a wavelength of 900 nm in xylene with an extinction value of 0.19 AU for 10 mg/L.

Example 3

Synthesis of
1,4,5,8-tetra(phenylamino)anthraquinone

A mixture of 10.87 g of 1,4,5,8-tetrachloroanthraquinone, 50 g of aniline, 13.4 g of potassium acetate, 1.24 g of copper sulfate, and 3.41 g of benzyl alcohol was heated to 130° C. under nitrogen and maintained at this temperature for 6.5 hours, followed by another holding period at 170° C. for 6 hours. The reaction mixture was cooled to ambient temperature and the precipitate was filtered to give black solids. Recrystallization of the crude product from toluene afforded 6.0 g of a dark green crystalline material (>95% purity with the structure confirmed by proton NMR as the desired product: 1,4,5,8-tetra(phenylamino)anthraquinone. This material had a maximum absorption band ($\lambda_{max}$) at a wavelength of 750 nm in toluene. The molar extinction coefficient ($\epsilon$) was determined to be ~30,500.

Example 4

Synthesis of
1,4,5,8-tetra(4-n-butylphenylamino)anthraquinone

A mixture of 10.87 g of 1,4,5,8-tetrachloroanthraquinone and 95 g of 4-n-butylaniline was allowed to react at 190° C. for 12 hours. The reaction mixture was then cooled to 70° C. and diluted with an equal amount of ethanol. On standing and further cooling to ambient temperature, some precipitate was formed. The mixture was filtered, washed and recrystallized from xylenes/isopropanol to give 6.6 g of a dark green crystalline material (>95% purity) with the structure confirmed by proton NMR as the desired product of 1,4,5,8-tetra(4-n-butylphenylamino)anthraquinone. This material had a maximum absorption band ($\lambda_{max}$) at a wavelength of 762 nm in toluene. The molar extinction coefficient ($\epsilon$) was determined to be ~36,900.

Example 5

Degradation of Lubricant Oil and Marker Under
High Heat and Oxidative Conditions A commercial motor oil (5W-30) containing 100 ppm of 1,4-di(2-ethylhexylamino)-2,3-dicyano-5,8-dihydroxyanthraquinone, 25 ppm Cu++, 10 ppm organic peroxide, 10 ppm toluenesulfonic acid, was heated to 165-170° C. with air bubbling for 48 hours. Spectroscopic determination of the marker after heat aging was done in the NIR at 800 nm. The results before and after the above heat and oxidation testing are summarized as follows:

|  | Before Heat-Aging | After Heat-Aging |
|---|---|---|
| Viscosity (Brookfield #2/30 rpm, 20° C.) | 12.8 cp | 16.1 cp |
| TAN (Total Acid #, mg KOH/g substrate) | 0 | 4.9 |
| Marker Conc. | 100 ppm | ~0 ppm |

These results demonstrate that the marker degrades along with the oil during heat aging, so that the marker concentration can be correlated with oil degradation.

Example 6

Synthesis of 1,4-di(2-ethylhexylamino)-2,3-dicyano-5,8-dihydroxyanthraquinone

A mixture of 36.3 parts of 1,4-di(2-ethylhexylamino)-5,8-dihydroxyanthraquinone (derived from Example 7), 14.8 parts of NaCN, 10 parts of $NH_4HCO_3$, and 140 parts of dimethyl sulfoxide (DMSO) was allowed to react at 90-95° C. for 6 hours to give 1,4-di(2-ethylhexylamino)-2,3-dicyano-5,8-dihydroxyanthraquinone. This material has a maximum absorption band ($\lambda_{max}$) at a wavelength of 809 nm in xylene. (Ref: JP62015260, JP61291652)

Example 7

Synthesis of 1,4-di-(2-ethylhexylamino)-5,8-dihydroxyanthraquinone

A mixture of leuco-1,4,5,8-tetrahydroxyanthraquinone (5.91 g), sodium dithionite (1.09 g) and 1-hexanol (175.2 g) was stirred while adding 2-ethylhexylamine (24.08 g). The mixture was heated to reflux (148-152° C.), maintained at reflux for 6-6.5 hours, and then cooled to ambient temperature. The precipitate was collected and washed thoroughly with methanol and water, and dried. The yield of dried isolated product was 7.0 g. Approximately another 1.9 g was present in the mother liquor, for a total yield of 8.9 g (90%). The structure of the molecule was confirmed with proton NMR. This material has a maximum absorption band ($\lambda_{max}$) at a wavelength of 692 nm in xylene, or 688 nm in cyclohexane, with an extinction value of 0.640 AU in xylene and 0.660 AU in cyclohexane for a 10 mg/L solution.

The invention claimed is:

1. A method for monitoring degradation of lubricating oils; said method comprising steps of:
(a) adding to a lubricating oil at least one compound having formula (I)

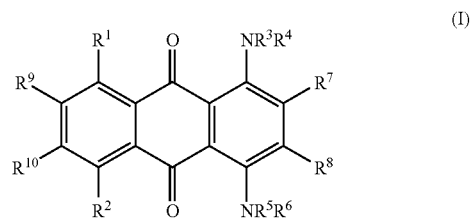

wherein $R^1$ and $R^2$ independently are hydrogen, hydroxy, $OR^{11}$, amino or $NR^{11}R^{12}$; $R^3$ and $R^5$ independently are alkyl, aryl, aralkyl, heteroalkyl or heterocyclic; $R^4$ and $R^6$ independently are hydrogen or alkyl; $R^7$, $R^8$, $R^9$ and $R^{10}$ independently are cyano, nitro, amide, carboxyl, ester, alkyl or hydrogen; $R^{11}$ is alkyl, aryl, aralkyl, heteroalkyl, heterocyclic or alkanoyl; $R^{12}$ is hydrogen or alkyl; provided that said at least one compound of formula (I) has at least one substituent selected from among cyano, nitro, hydroxy, hydroxyalkyl, amide, carboxyl, ester and unsaturated alkyl;

(b) measuring a spectroscopic property of the oil to determine degradation of said at least one compound by comparing absorption intensity displayed by a cyano, nitro, hydroxyl, hydroxyalkyl, amide, carboxyl, ester or unsaturated alkyl substituent with absorption intensity of the cyano, nitro, hydroxy, hydroxyalkyl, amide, carboxyl, ester or unsaturated alkyl substituent when said at least one compound was first introduced into the lubricating oil, and determining a fraction of molecules containing the cyano, nitro, hydroxy, hydroxyalkyl, amide, carboxyl, ester or unsaturated alkyl substituent that have been degraded; and (c) correlating said fraction with degradation of the lubricating oil.

2. The method of claim 1 in which said at least one compound of formula (I) has at least one substituent selected from among cyano, nitro, carboxyl and hydroxyalkyl.

3. The method of claim 1 in which said at least one compound is present in an amount from 0.5 ppm to 5,000 ppm.

4. The method of claim 3 in which the spectroscopic property is absorption of electromagnetic radiation in a mid-IR or NIR range.

5. The method of claim 4 in which said at least one compound is present in an amount from 5 ppm to 2,000 ppm.

6. The method of claim 1 in which said at least one compound is substituted by at least one group selected from among $C_2$-$C_{20}$ unsubstituted saturated acyclic alkyl groups, aryl groups substituted by at least one $C_2$-$C_{20}$ alkyl group, aromatic heterocyclic groups substituted by at least one $C_2$-$C_{20}$ alkyl group and $C_5$-$C_8$ cyclic alkyl groups.

7. The method of claim 6 in which said at least one compound is present in an amount from 5 ppm to 2,000 ppm.

8. The method of claim 7 in which the spectroscopic property is absorption of electromagnetic radiation in a mid-IR or NIR range.

9. A method for monitoring degradation of lubricating oils; said method comprising steps of:
(a) adding to a lubricating oil at least one compound having formula (I) in an amount from 5 ppm to 5,000 ppm

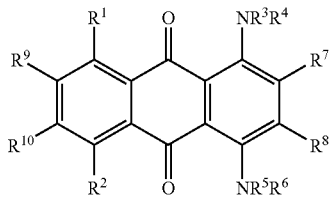

wherein $R^1$ and $R^2$ independently are hydrogen, hydroxy, $OR^{11}$, amino or $NR^{11}R^{12}$; $R^3$ and $R^5$ independently are alkyl, aryl, aralkyl, heteroalkyl or heterocyclic; $R^4$ and $R^6$ independently are hydrogen or alkyl; $R^7$, $R^8$, $R^9$ and $R^{10}$ independently are cyano, nitro, amide, carboxyl, ester, alkyl or hydrogen; $R^{11}$ is alkyl, aryl, aralkyl, heteroalkyl, heterocyclic or alkanoyl; $R^{12}$ is hydrogen or alkyl;

(b) measuring absorption of electromagnetic radiation in a mid-IR or NIR range by the oil to determine degradation of said at least one compound;

wherein said at least one compound of formula (I) has at least one substituent selected from among cyano, nitro, carboxyl and hydroxyalkyl; and (c) correlating said degradation of said at least one compound with degradation of the lubricating oil.

10. The method of claim 9 in which said at least one compound is substituted by at least one group selected from among $C_2$-$C_{20}$ unsubstituted saturated acyclic alkyl groups, aryl groups substituted by at least one $C_2$-$C_{20}$ alkyl group, aromatic heterocyclic groups substituted by at least one $C_2$-$C_{20}$ alkyl group and $C_5$-$C_8$ cyclic alkyl groups.

* * * * *

UNITED STATES PATENT AND TRADEMARK OFFICE
CERTIFICATE OF CORRECTION

PATENT NO. : 7,635,596 B2
APPLICATION NO. : 11/269788
DATED : December 22, 2009
INVENTOR(S) : Banavali et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1035 days.

Signed and Sealed this

Ninth Day of November, 2010

David J. Kappos
*Director of the United States Patent and Trademark Office*